(12) United States Patent
Wraith et al.

(10) Patent No.: US 7,071,297 B2
(45) Date of Patent: Jul. 4, 2006

(54) TOLEROGENIC PEPTIDES FROM MYELIN BASIC PROTEIN

(75) Inventors: David Cameron Wraith, Bristol (GB); Heather Barbara Streeter, Bristol (GB); Mary Ponsford, Bristol (GB); Graziella Mazza, Bristol (GB)

(73) Assignee: Apitope Technology (Bristol) Limited (GB)

( * ) Notice: Subject to any disclaimer, the term of this patent is extended or adjusted under 35 U.S.C. 154(b) by 0 days.

(21) Appl. No.: 10/900,032

(22) Filed: Jul. 27, 2004

(65) Prior Publication Data

US 2005/0058643 A1 Mar. 17, 2005

Related U.S. Application Data

(63) Continuation-in-part of application No. PCT/GB03/00399, filed on Jan. 30, 2003.

(30) Foreign Application Priority Data

Feb. 1, 2002 (GB) .............................................. 0202399

(51) Int. Cl.
*A61K 38/00* (2006.01)
*A61K 38/08* (2006.01)

(52) U.S. Cl. ........................... 530/300; 530/326; 514/12
(58) Field of Classification Search ................ 530/300, 530/326; 514/12
See application file for complete search history.

(56) References Cited

U.S. PATENT DOCUMENTS 5,858,980 A   1/1999   Weiner et al. ................. 514/13

FOREIGN PATENT DOCUMENTS

| IL | 146016 | * | 10/2001 |
|---|---|---|---|
| WO | WO 9530435 A2 | * | 11/1995 |
| WO | WO 96/12737 | | 5/1996 |
| WO | WO 02/16410 A2 | | 2/2002 |

OTHER PUBLICATIONS

Vergelli, M., et al., "T cell response to myelin basic protein in the context of the multiple sclerosis–associated HLA–DR15 haplotype: peptide binding, immunodominance and effector functions of T cells", *Journal of Neuroimmunology*, (1977), pp. 195–203.

Vogt, Anne B., et al., "Ligand Motifs of HLA–DRB5*0101 and DRB1*1501 Molecules Delineated from Self–Peptides.", *The Journal of Immunology*, (1994), pp 1665–1673.

* cited by examiner

*Primary Examiner*—Robert A. Wax
*Assistant Examiner*—Suzanne M. Mayer
(74) *Attorney, Agent, or Firm*—Schwegman, Lundberg, Woessner & Kluth, P.A.

(57) ABSTRACT

There is provided a peptide that is capable of binding to an MHC class I or II molecule without further processing (i.e., an apitope), which comprises a portion of the region 131–158 of myelin basic protein. In particular, there is provided an apitope which is selected from the following myelin basic protein peptides: 134–148, 135–149, 136–150, 137–151, 138–152, 139–153, 140–154.

There is also provided the use of such a peptide in a pharmaceutical composition and a method to treat and/or prevent a disease using such a peptide.

16 Claims, 4 Drawing Sheets

SEQUENCE LISTING

```
<160> NUMBER OF SEQ ID NOS: 7

<210> SEQ ID NO 1
<211> LENGTH: 15
<212> TYPE: PRT
<213> ORGANISM: Homo sapiens

<400> SEQUENCE: 1

Tyr Lys Ser Ala His Lys Gly Phe Lys Gly Val Asp Ala Gln Gly
1               5                   10                  15

<210> SEQ ID NO 2
<211> LENGTH: 15
<212> TYPE: PRT
<213> ORGANISM: Homo sapiens

<400> SEQUENCE: 2

Lys Ser Ala His Lys Gly Phe Lys Gly Val Asp Ala Gln Gly Thr
1               5                   10                  15

<210> SEQ ID NO 3
<211> LENGTH: 15
<212> TYPE: PRT
<213> ORGANISM: Homo sapiens

<400> SEQUENCE: 3

Ser Ala His Lys Gly Phe Lys Gly Val Asp Ala Gln Gly Thr Leu
1               5                   10                  15

<210> SEQ ID NO 4
<211> LENGTH: 15
<212> TYPE: PRT
<213> ORGANISM: Homo sapiens

<400> SEQUENCE: 4
```

```
Ala His Lys Gly Phe Lys Gly Val Asp Ala Gln Gly Thr Leu Ser
 1               5                  10                  15

<210> SEQ ID NO 5
<211> LENGTH: 15
<212> TYPE: PRT
<213> ORGANISM: Homo sapiens

<400> SEQUENCE: 5

His Lys Gly Phe Lys Gly Val Asp Ala Gln Gly Thr Leu Ser Lys
 1               5                  10                  15

<210> SEQ ID NO 6
<211> LENGTH: 15
<212> TYPE: PRT
<213> ORGANISM: Homo sapiens

<400> SEQUENCE: 6

Lys Gly Phe Lys Gly Val Asp Ala Gln Gly Thr Leu Ser Lys Ile
 1               5                  10                  15

<210> SEQ ID NO 7
<211> LENGTH: 15
<212> TYPE: PRT
<213> ORGANISM: Homo sapiens

<400> SEQUENCE: 7

Gly Phe Lys Gly Val Asp Ala Gln Gly Thr Leu Ser Lys Ile Phe
 1               5                  10                  15
```

TOLEROGENIC PEPTIDES FROM MYELIN BASIC PROTEIN

CLAIM OF PRIORITY

This application is a continuation-in-part application under 35 U.S.C. § 111(a) of International Application No. PCT/GB03/00399, filed Jan. 30, 2003 and published in English as WO 03/064464 A1 on Aug. 7, 2003, which claims priority to Great Britain Application Serial No. 0202399.2 filed on Feb. 1, 2002, the disclosures of which applications and publication are incorporated by reference herein.

FIELD OF INVENTION

The present invention relates to peptides from myelin basic protein. In particular, the invention relates to peptides which comprise a portion of the region 131–158 of myelin basic protein and their use in the treatment and/or prevention of a disease.

BACKGROUND OF THE INVENTION

In an adaptive immune response, T lymphocytes are capable of recognising internal epitopes of a protein antigen. Antigen presenting cells (APC) take up protein antigens and degrade them into short peptide fragments. A peptide may bind to a major histocompatability complex (MHC) class I or II molecule inside the cell and be carried to the cell surface. When presented at the cell surface in conjunction with an MHC molecule, the peptide may be recognised by a T cell (via the T cell receptor (TCR)), in which case the peptide is a T cell epitope.

T cell epitopes play a central role in the adaptive immune response to any antigen, whether self or foreign. The central role played by T cell epitopes in hypersensitivity diseases (which include allergy, autoimmune diseases and transplant rejection) has been demonstrated through the use of experimental models. It is possible to induce inflammatory or allergic diseases by injection of synthetic peptides (based on the structure of T cell epitopes) in combination with adjuvant.

By contrast, it has been shown to be possible to induce immunological tolerance towards particular peptide epitopes by administration of peptide epitopes in soluble form. Administration of soluble peptide antigens has been demonstrated as an effective means of inhibiting disease in experimental autoimmune encephalomyelitis (EAE—a model for multiple sclerosis (MS)) (Metzler and Wraith (1993) Int. Immunol. 5:1159–1165; Liu and Wraith (1995) Int. Immunol. 7:1255–1263; Anderton and Wraith (1998) Eur. J. Immunol. 28:1251–1261); and experimental models of arthritis, diabetes, and uveoretinitis (reviewed in Anderton and Wraith (1998) as above). This has also been demonstrated as a means of treating an ongoing disease in EAE (Anderton and Wraith (1998) as above).

The use of tolerogenic peptides to treat or prevent disease has attracted considerable attention. One reason for this is that it has been shown that certain tolerogenic epitopes can down-regulate responses of T cells for distinct antigens within the same tissue. This phenomenon, known as "bystander suppression" means that it should be possible to induce tolerance to more than one epitope (for example, all epitopes) within a given antigen, and to more than one antigen for a given disease, using a particular tolerogenic peptide (Anderton and Wraith (1998) as above). This would obviate the need to identify all of the pathogenic antigens within a particular disease.

Peptides are also a favourable option for therapy because of their relatively low cost and the fact that peptide analogues can be produced with altered immunological properties. Peptides may thus be modified to alter their interactions with either MHC or TCR.

One possible problem with this approach is that it has been shown that not all peptides which act as T cell epitopes are capable of inducing tolerance. The myelin basic protein (MBP) peptide 89–101 is an immunodominant antigen after immunisation and is also a very effective immunogen both in terms of priming for T cell reactivity and induction of EAE. However, this peptide has been shown to be ineffective at inducing tolerance when administered in solution (Anderton and Wraith (1998), as above).

A number of explanations for the observed hierarchy in the ability of T cell epitopes to induce tolerance have been proposed (reviewed in Anderton and Wraith (1998) as above). In particular, it has been proposed that there is a correlation between the affinity of the peptide for the MHC and tolerogenicity (Liu and Wraith (1995) as above), but this does not tally with some of the observations. For example, MBP[89–101], which is not tolerogenic, binds to I-A$^S$ with relatively high affinity. It is thus not straightforward to predict which peptides will induce tolerance.

The present inventors have shown that if a peptide epitope is of an appropriate size to be presented by immature APC without antigen processing, it can induce immunological tolerance (International patent application number PCT/GB01/03702). The observation that some T cell epitopes are tolerogenic and others are incapable of inducing tolerance can therefore be explained by the fact that some epitopes require further processing before they are capable of being presented by an MHC molecule. These epitopes which require further processing do not induce tolerance when administered in a soluble form, despite their capacity to induce disease when injected in combination with adjuvant.

The epitopes which do not require further processing are capable of inducing tolerance, and have been termed "apitopes" (Antigen Processing Independent epiTOPES) by the inventors.

SUMMARY OF THE INVENTION

The present inventors have examined the region 131–158 of MBP, and found a number of peptides which can be presented by fixed antigen presenting cells to T-cells. These peptides are defined as apitopes, because they are capable of binding to MHC class I or II molecules without further processing, i.e., peptides capable of binding to an MHC class I or MHC class II molecule independent of antigen processing.

In a first aspect, therefore, the present invention provides an apitope which comprises a portion of the region 131–158 of myelin basic protein.

The present inventors have also identified two minimal epitopes in this region which are recognised by particular T-cell clones. The peptide may comprise one or both of these epitopes which are MBP 142–152 and 140–148.

In one embodiment the peptide is selected from the following myelin basic protein peptides: 134–148, 135–149, 136–150, 137–151, 138–152, 139–153, 140–154, and 134–154.

In a second aspect, the present invention provides a pharmaceutical composition comprising one or more peptide(s) according to the first aspect of the application.

In a third aspect, the present invention provides a method for treating and/or preventing a disease in a subject in need of same which comprises the step of administering a peptide according to the first aspect of the invention to the subject.

In one embodiment, the present invention provides a therapeutic composition having an effective immunosuppressive amount of an isolated and purified peptide comprising a portion of region 131–158 of myelin basic protein, wherein the peptide is capable of binding to an MHC class I molecule or an MHC class II molecule without further processing. For example, the invention provides such a composition wherein the amount is effective to induce immunological tolerance in a mammal. In one embodiment of the invention, the portion is 134–148 (SEQ ID NO:1), 135–149 (SEQ ID NO:2), 136–150 (SEQ ID NO:3), 137–151 (SEQ ID NO:4), 138–152 (SEQ ID NO:5), 139–153 (SEQ ID NO:6) or 140–154 (SEQ ID NO:7). In another embodiment, the portion is 140–154 (SEQ ID NO:7). In another embodiment, the present invention provides such a composition in combination with a pharmaceutically acceptable carrier.

The present invention also provides the use of a peptide according to the first aspect of the invention in the manufacture of a medicament for use in the treatment and/or prevention of a disease.

The peptides of the present invention are useful in the prevention and/or treatment of multiple sclerosis. One embodiment of the present invention provides a method for treating or preventing multiple scelorsis in a subject in need thereof, which method involves administering, for example, intranasally, to the subject an effective amount of an isolated and purified peptide comprising a portion of region 131–158 of myelin basic protein, for example, 140–154 (SEQ ID NO:7), wherein the peptide is capable of binding to an MHC class I molecule or class II molecule and inducing immunological tolerance.

DETAILED DESCRIPTION OF INVENTION

Figure 1:
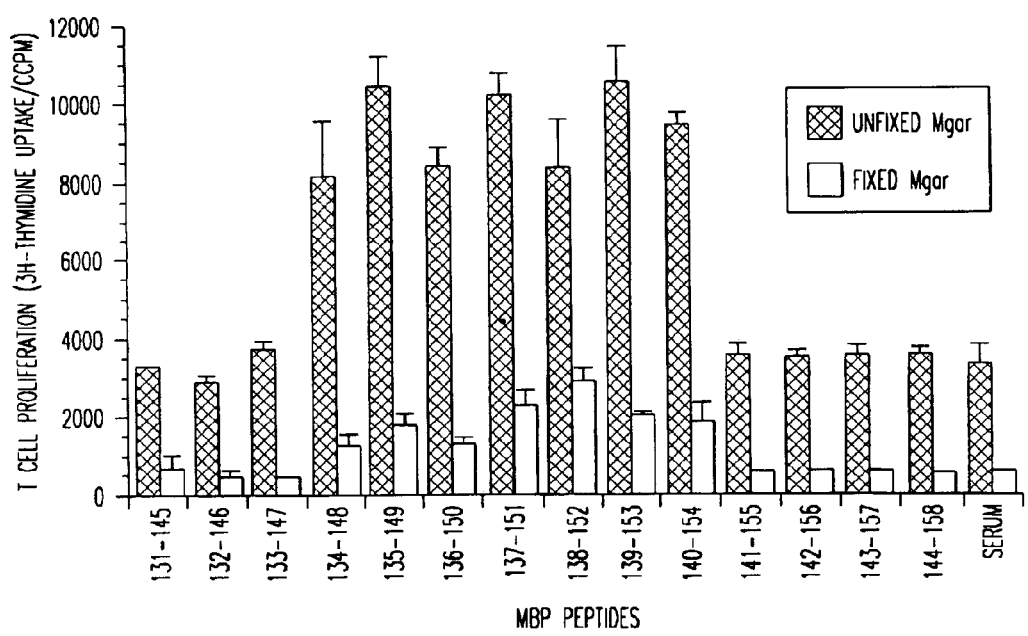
FIG. 1 shows the response of T cell clone MS60:D2 to presentation of nested MBP peptides in the region 131–158 by APC.

In a first aspect, the present invention relates to a peptide. Peptides

The term "peptide" is used in the normal sense to mean a series of residues, typically L-amino acids, connected one to the other typically by peptide bonds between the α-amino and carboxyl groups of adjacent amino acids The term includes modified peptides and synthetic peptide analogues.

A peptide of the present invention may be any length that is capable of binding to an MHC class I or II molecule without further processing.

Peptides that bind to MHC class I molecules are typically 7 to 13, more usually 8 to 10 amino acids in length. The binding of the peptide is stabilised at its two ends by contacts between atoms in the main chain of the peptide and invariant sites in the peptide-binding groove of all MHC class I molecules. There are invariant sites at both ends of the groove which bind the amino and carboxy termini of the peptide. Variations is peptide length are accommodated by a kinking in the peptide backbone, often at proline or glycine residues that allow the required flexibility.

Peptides which bind to MHC class II molecules are typically between 8 and 20 amino acids in length, more usually between 10 and 17 amino acids in length, and can be much longer. These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

The peptide of the present invention may be made using chemical methods (Peptide Chemistry, A practical Textbook. Mikos Bodansky, Springer-Verlag, Berlin.). For example, peptides can be synthesized by solid phase techniques (Roberge J Y et al (1995) Science 269: 202–204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from myelin basic protein. The composition of a peptide may be confirmed by amino acid analysis or sequencing (e.g., the Edman degradation procedure).

The peptide of the invention is derivable from region 131–158 of MBP. In one embodiment, the peptide is derivable from a fragment of the antigen which arises by natural processing of the antigen by an APC.

For practical purposes, there are various other characteristics which the peptide should show. For example, the peptide should be soluble at a concentration which permits its use in vivo. In one embodiment, the peptide should be soluble at concentrations of up to 0.5 mg/ml, in another embodiment, the peptide should be soluble at concentrations of up to 1 mg/ml, and in yet another embodiment, the peptide should be soluble at concentrations of up to 5 mg/ml.

For intranasal administration the maximum volume of dose which can be taken up using current procedures is approximately 200 µl per nostril. If the peptide is soluble at 1 mg/ml, a double dose to each nostril enables 800 µg to be given to the patient. It is unusual to give more that 5 mg in any individual dose.

It is also important that the peptide is sufficiently stable in vivo to be therapeutically useful. The present inventors have found that in vivo, 30 minutes after administration the total amount of a test peptide drops to about 50%, 4 hours after administration the amount drops to about 30%, but that after 5 days the peptide is still detectable (at about 5%). The half-life of the peptide in vivo should be at least 10 minutes, in one embodiment at least 30 minutes, in another embodiment at least 4 hours, and in yet another embodiment, at least 24 hours.

The present inventors have found that following intranasal administration, the amount of peptide in the draining lymph node peaks at about 4 hrs following administration, however peptide is still detectable (at levels of about 5% maximum) after 5 days. Preferably the peptide is sufficiently stable to be present at a therapeutically active concentration in the draining lymph node for long enough to exert a therapeutic effect.

The peptide should also demonstrate good bioavailability in vivo. The peptide should maintain a conformation in vivo which enables it to bind to an MHC molecule at the cell surface without due hindrance.

Myelin Basic Protein (MBP)

MBP is an antigen from myelin, which has been previously characterised and sequenced (Roth et al., *J. Neurosci. Res.*, 17: 321–328 (1987); Accession number M30516).

The peptides of the present invention are derivable from MBP region 131–158.

In one embodiment, the peptide is or comprises one or more of the minimal T-cell epitopes in the region, for example the minimal epitope MBP142–152 or 140–148.

In one embodiment, the peptide is selected from the following myelin basic protein peptides:

| MBP peptide | Sequence | |
|---|---|---|
| 134-148 | YKSAHKGFKGVDAQG | (SEQ ID NO:1) |
| 135-149 | KSAHKGFKGVDAQGT | (SEQ ID NO:2) |
| 136-150 | SAHKGFKGVDAQGTL | (SEQ ID NO:3) |
| 137-151 | AHKGFKGVDAQGTLS | (SEQ ID NO:4) |
| 138-152 | HKGFKGVDAQGTLSK | (SEQ ID NO:5) |
| 139-153 | KGFKGVDAQGTLSKI | (SEQ ID NO:6) |
| 140-154 | GFKGVDAQGTLSKIF | (SEQ ID NO:7) |

Antigen Processing Independent Epitopes (APITOPES)

The peptide of the present invention is capable of binding to an MHC class I or II molecule (in the peptide-binding groove) without further processing. Such peptides are known herein as "apitopes" (Antigen Processing Independent epiTOPES).

Cell surface presentation of peptides derived from a given antigen is not random and tends to be dominated by a small number of frequently occurring epitopes. The dominance of a particular peptide will depend on many factors, such as relative affinity for binding the MHC molecule, spatio-temporal point of generation within the APC and resistance to degradation. The epitope hierarchy for an antigen can change with progression of an immune response, which has important implications for self-tolerance and autoimmunity. Immunodominant determinant regions are likely to be good tolerogens. Hence, in one embodiment of the present invention, the apitope of the present invention is based on a dominant epitope.

However, after a primary immune response to the immunodominant peptides, epitope "spreading" may occur to sub-dominant determinants (Lehmann et al (1992) Nature 358:155–157). Presentation of sub-dominant epitopes may be important in triggering autoimmunity. The apitope of the present invention may, therefore be based on a subdominant epitope.

For any given antigen, cryptic epitopes may also exist. Cryptic epitopes are those which can stimulate a T cell response when administered as a peptide but which fail to produce such a response when administered as a whole antigen. It may be that during processing of the antigen into peptides in the APC the cryptic epitope is destroyed.

A cryptic epitope may act as an apitope in vitro, in that it may be capable of binding to an MHC molecule without further processing, and inducing anergy in a T cell which recognises the cryptic epitope. However, such an apitope would be unlikely to be therapeutically useful because it should be incapable of tolerising T cells which recognise a naturally processed epitope of the antigen.

Epitopes for an antigen may be identified by measuring the T cell response to overlapping peptides spanning the entire antigen (see below) when presented by APC. Such studies usually result in "nested sets" of peptides, and the minimal epitope for a particular T cell line/clone can be assessed by measuring the response to truncated peptides.

It cannot be assumed that a minimal epitope of an antigen will behave as an apitope. It may well be that amino acids flanking the minimal epitope will be required for optimal binding to the MHC. The apitope should be designed to cover the possibility that there may be subtle differences between the minimal epitopes of different T cell clones.

It should be emphasised that it may not be possible to identify an apitope for all epitopes. There is clear evidence that some epitopes bind MHC in a way that is dependent on MHC-loading in endosomes and hence require processing (Viner et al (1995) Proc. Natl. Acad. Sci. 92:2214–2218). This is another reason why one cannot assume that each minimal epitope will inevitably behave as an apitope.

Identification of Peptides Containing T Cell Epitopes

There are a number of methods known in the art to identify the T cell epitopes within a given antigen.

Naturally processed epitopes may be identified by mass spectrophotometric analysis of peptides eluted from antigen-loaded APC. These are APC that have either been encouraged to take up antigen, or have been forced to produce the protein intracellularly by transformation with the appropriate gene. Typically APC are incubated with protein either in solution or suitably targeted to the APC cell surface. After incubation at 37° C. the cells are lysed in detergent and the class II protein purified by, for example affinity chromatography. Treatment of the purified MHC with a suitable chemical medium (for example, acid conditions) results in the elution of peptides from the MHC. This pool of peptides is separated and the profile compared with peptide from control APC treated in the same way. The peaks unique to the protein expressing/fed cells are analysed (for example by mass spectrometry) and the peptide fragments identified. This procedure usually generates information about the range of peptides (usually found in "nested sets") generated from a particular antigen by antigen processing.

Another method for identifying epitopes is to screen a synthetic library of peptides which overlap and span the length of the antigen in an in vitro assay. For example, peptides which are 15 amino acids in length and which overlap by 5 or 10 amino acids may be used. The peptides are tested in an antigen presentation system which comprises antigen presenting cells and T cells. For example, the antigen presentation system may be a murine splenocyte preparation, a preparation of human cells from tonsil or PBMC.

Alternatively, the antigen presentation system may comprise a particular T cell line/clone and/or a particular antigen presenting cell type.

T cell activation may be measured via T cell proliferation (for example using $^3$H-thymidine incorporation) or cytokine production. Activation of TH 1-type CD4+ T cells can, for example be detected via IFNγ production which may be detected by standard techniques, such as an ELISPOT assay.

Overlapping peptide studies usually indicate the area of the antigen in which an epitope is located. The minimal epitope for a particular T cell can then be assessed by measuring the response to truncated peptides. For example if a response is obtained to the peptide comprising residues 1–15 in the overlapping library, sets which are truncated at both ends (i.e. 1–14, 1–13, 1–12 etc. and 2–15, 3–15, 4–15 etc.) can be used to identify the minimal epitope.

Antigen Processing Independent Presentation Systems (APIPS)

Once an epitope has been identified, the next step is to investigate whether it also behaves as an apitope.

An apitope must be presented to T cells without the need for antigen processing. Having identified peptides containing T cell epitopes, apitopes may be identified using a processing free system. Truncated peptides and peptide analogues may be tested for activation using an antigen processing independent presentation system (APIPS). Examples of APIPS Include:
a) fixed APC (with or without antibodies to CD28);
b) Lipid membranes containing Class I or II MHC molecules (with or without antibodies to CD28); and
c) purified natural or recombinant MHC in plate-bound form (with or without antibodies to CD28).

It is known to use fixed APC to investigate T cell responses, for example in studies to investigate the minimal epitope within a polypeptide, by measuring the response to truncated peptides (Fairchild et al (1996) Int. Immunol. 8:1035–1043). APC may be fixed using, for example formaldehyde (usually paraformaldehyde) or glutaraldehyde.

Lipid membranes (which may be planar membranes or liposomes) may be prepared using artificial lipids or may be plasma membrane/microsomal fractions from APC.

In use, the APIPS may be applied to the wells of a tissue culture plate. Peptide antigens are then added and binding of the peptide to the MHC portion of the APIPS is detected by addition of selected T cell lines or clones. Activation of the T cell line or clone may be measured by any of the methods known in the art, for example via $^3$H-thymidine incorporation or cytokine secretion.

Tolerance

The peptides of the present invention should be capable of inducing tolerance to MBP as they are apitopes for this antigen.

As used herein, the term "tolerogenic" means capable of inducing tolerance.

Tolerance is the failure to respond to an antigen. Tolerance to self antigens is an essential feature of the immune system, when this is lost, autoimmune disease can result. The adaptive immune system must maintain the capacity to respond to an enormous variety of infectious agents while avoiding autoimmune attack of the self antigens contained within its own tissues. This is controlled to a large extent by the sensitivity of immature T lymphocytes to apoptotic cell death in the thymus (central tolerance). However, not all self antigens are detected in the thymus, so death of self-reactive thymocytes remains incomplete. There are thus also mechanisms by which tolerance may be acquired by mature self-reactive T lymphocytes in the peripheral tissues (peripheral tolerance). A review of the mechanisms of central and peripheral tolerance is given in Anderton et al (1999) (*Immunological Reviews* 169:123–137).

Tolerance may result from or be characterised by the induction of anergy in at least a portion of CD4+ T cells. In order to activate a T cell, a peptide must associate with a "professional" APC capable of delivering two signals to T cells. The first signal (signal 1) is delivered by the MHC-peptide complex on the cell surface of the APC and is received by the T cell via the TCR. The second signal (signal 2) is delivered by costimulatory molecules on the surface of the APC, such as CD80 and CD86, and received by CD28 on the surface of the T cell. It is thought that when a T cell receives signal 1 in the absence of signal 2, it is not activated and, in fact, becomes anergic. Anergic T cells are refractory to subsequent antigenic challenge, and may be capable of suppressing other immune responses. Anergic T cells are thought to be involved in mediating T cell tolerance.

Without wishing to be bound by theory, the present inventors predict that peptides which require processing before they can be presented in conjunction with MHC molecules do not induce tolerance because they have to be handled by mature antigen presenting cells. Mature antigen presenting cells (such as macrophages, B cells and dendritic cells) are capable of antigen processing, but also of delivering both signals 1 and 2 to a T cell, leading to T cell activation. Apitopes, on the other hand, will be able to bind class II MHC on immature APC. Thus they will be presented to T cells without costimulation, leading to T cell anergy and tolerance.

Of course, apitopes are also capable of binding to MHC molecules at the cell surface of mature APC. However, the immune system contains a greater abundance of immature than mature APC (it has been suggested that less than 10% of dendritic cells are activated, Summers et al. (2001) Am. J. Pathol. 159: 285–295). The default position to an apitope will therefore be anergy/tolerance, rather than activation.

It has been shown that, when tolerance is induced by peptide inhalation, the capacity of antigen-specific CD4+ T cells to proliferate is reduced. Also, the production of IL-2, IFN-γ and IL4 production by these cells is down-regulated, but production of IL-10 is increased. Neutralisation of IL-10 in mice in a state of peptide-induced tolerance has been shown to restore completely susceptibility to disease. It has been proposed that a population of regulatory cells persist in the tolerant state which produce IL-10 and mediate immune regulation (Burkhart et al (1999) Int. Immunol. 11:1625–1634).

The induction of tolerance can therefore be monitored by various techniques including:
(a) reduced susceptibility to contract the disease for which the peptide is a target epitope in vivo;
(b) the induction of anergy in CD4+ T cells (which can be detected by subsequent challenge with antigen in vitro);
(c) changes in the CD4+ T cell population, including
  (i) reduction in proliferation;
  (ii) down-regulation in the production of IL-2, IFN-γ and IL-4; and
  (iii) increase in the production of IL-10.

Target Diseases

The peptide of the invention may be used in the treatment and/or prevention of a disease.

The peptides of the present invention are particularly useful in the treatment and/or prevention of multiple sclerosis (MS). Multiple sclerosis (MS) is a chronic inflammatory disease characterised by multiple demyelinating lesions disseminated throughout the CNS white matter and occurring at various sites and times (McFarlin and McFarland, 1982 New England J. Medicine 307:1183–1188 and 1246–1251). MS is thought to be mediated by autoreactive T cells.

MBP is immunogenic and MBP-specific T lymphocytes have encephalitogenic activity in animals (Segal et al., 1994

J. Neuroimmunol. 51:7–19; Voskuhl et al., 1993 J. Neuroimmunol 42:187–192; Zamvil et al., 1985 Nature 317:355–8).

Pharmaceutical Composition

In a second aspect, the present invention relates to a pharmaceutical composition comprising one or more peptide(s) of the first aspect of the invention. The composition may also comprise one or more apitopes from another region of MBP or from a different antigen.

The present inventors predict that, despite "bystander suppression" it may be necessary to target a number of different T cell clones in order to induce tolerance effectively. Hence a plurality of peptides may be administered to an individual in order to prevent or treat a disease.

The pharmaceutical composition may, for example comprise between 1 and 50 apitopes, preferably between 1 and 15 apitopes. If there is more than one apitope, preferably the apitopes are either all able to bind to MHC class I, or all able to bind MHC class II, without further processing.

Where there are two or more apitopes, the pharmaceutical composition may be in the form of a kit, in which some or each of the apitopes are provided separately for simultaneous, separate or sequential administration.

Alternatively (or in addition) if the pharmaceutical composition (or any part thereof) is to be administered in multiple doses, each dose may be packaged separately.

The pharmaceutical composition may comprise a therapeutically or prophylactically effective amount of the or each apitope and optionally a pharmaceutically acceptable carrier, diluent or excipient.

Also, in the pharmaceutical compositions of the present invention, the or each apitope may be admixed with any suitable binder(s), lubricant(s), suspending agent(s), coating agent(s), or solubilising agent(s).

Administration

The peptide may be administered in soluble form in the absence of adjuvant.

Preferably the peptide is administered by a mucosal route.

Studies have shown that peptide, when given in soluble form intraperitoneally (i.p.), intravenously (i.v.) or intranasally (i.n.) or orally can induce T cell tolerance (Anderton and Wraith (1998) as above; Liu and Wraith (1995) as above; Metzler and Wraith (1999) Immunology 97:257–263). Preferably the peptide is administered intranasally.

Studies in mice have demonstrated that the duration of peptide administration required to induce tolerance depends on the precursor frequency of T cells in the recipient (Burkhart et al (1999) as above). In many experimental studies, it has been shown that repeated doses of peptide are required to induce tolerance (Burkhart et al (1999) as above). The exact dose and number of doses of peptide will therefore depend on the individual, however, in one embodiment, a plurality of doses is administered.

If a plurality of peptides is administered simultaneously, they may be in the form of a "cocktail" which is suitable for administration in single or multiple doses. Alternatively it may be preferably to give multiple doses but vary the relative concentrations of the peptides between doses.

In one embodiment of the invention, a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747–754 and Akdis et al (1998) J. Clin. Invest. 102:98–106).

EXAMPLES

The following examples serve to illustrate the present invention, but should not be construed as a limitation thereof. The invention particularly relates to the specific embodiments described in these examples.

Example 1

Identification of Apitopes Within MBP Region 134–154

Materials and Methods

Antigens

Human MBP is prepared from brain white matter as described by Deibler et al. (Deibler et al., 1972 Preparative Biochemistry 2:139), and its purity assessed by SDS-PAGE. MBP and *Mycobacterium tuberculosis* purified protein derivative (PPD) (UK Central Veterinary Laboratory, Surrey) are used in proliferative assays at previously determined optimal concentrations; the optimum concentration for each antigen is 20 µg/ml. A panel of 15-mer overlapping peptides spanning MBP region 131–158 are synthesized using standard F-moc chemistry on an Abimed AMS 422 multiple peptide synthesizer (Abimed, Langenfeld, Germany). Each peptide is displaced by 1 aa and overlapped by 14 aa.

Tissue Culture Medium

RPMI-1640 medium supplemented with 20 mM HEPES (Sigma, Poole, UK), penicillin (100 U/ml), streptomycin sulphate (100 mg/ml), and 4 mM L-glutamine (all from Life Technologies, Paisley, Scotland), is used as the tissue culture medium. Medium without serum is used for washing lymphoid cells and TCL. For all culture conditions and assays, medium is supplemented with 10% heat inactivated autologous plasma.

Generation of T Cell Clones

MBP-specific T cell lines (TCL) are generated from 8 MS patients and 2 healthy control donors. PBMC from each subject are separated as described above and plated out at $1\times10^6$ cells/ml in 6-well plates in the presence of MBP (50 µg/ml); a portion of PBMC from each subject is regularly frozen and stored for subsequent restimulations. Seven days later the cells are fed with fresh medium containing 2% IL-2 (Lymphocult-HT; Biotest LTD., Birmingham, UK), and on day 12 of culture all cells are restimulated with antigen, IL-2 and irradiated (2500 Rad) autologous PBMC as a source of antigen presenting cells (APC), at a cell ratio of 1T cell:5 APC. Cells are expanded in IL-2 every 3–4 days, and on day 14 are restimulated with antigen, IL-2 and PBMC, as described above. On the day of the first restimulation cells are examined for specific proliferation to MBP. Briefly, $2\times10^4$ T cells and $1\times10^5$ irradiated autologous PBMC are cultured in triplicate, in 96-well round-bottom plates, in the presence of MBP. Cells are cultured for 2 days and pulsed with ($^3$H)-Thymidine at 0.4 µCi/well during the last 18 hours of the culture. Cells are then harvested as described above, and a TCL is considered to be MBP-specific with a δcpm>1000 and a SI>3.

Following 3 restimulation/expansion cycles TCL are cloned using PHA (Sigma, Poole, Dorset, UK)) in the presence of autologous irradiated PBMC as APC. T cells are plated under limiting dilution conditions at 0.1 cell/well, 0.3 cell/well and 1 cell/well and cultured in Terasaki plates (Nunc International, Costar) with $1\times10^4$ irradiated PBMC, 5 µg/ml PHA, and 2% IL-2. After 10–12 days, growth-positive wells are expanded onto 96-well round-bottom plates, using $1\times10^5$ irradiated PBMC, 5 µg/ml PHA and IL-2. Three days later wells are fed with fresh medium containing IL-2, and on day 7 the clones are expanded onto 48-well plates using $5\times10^5$ irradiated PBMC, PHA and IL-2; at this point clones are tested in proliferation assays for specific responses to MBP. MBP-specific clones are expanded a week later onto 24-well plates, using 1×10⁶ irradiated PBMC with PHA or Dynabeads (Dynal, UK) and IL-2. The clones are maintained in 24-well plates using a 7–10 day restimulation/expansion cycle.

Proliferation Assay

Live or p-formaldehyde fixed Mgar (HLA-DR2+ve) cells were incubated with peptides in serum or in serum alone, together with T cells. The T cell proliferative response was measured by $^3$H-thymidine uptake as follows. Triplicate aliquots of 100 μl of each culture were grown in a 96-well round bottom microtitre plate for 48 hours, then pulsed with 0.4 μCi [$^3$H]-Thymidine (Amersham International, Amersham, UK). After 20 hours cells are harvested onto glass fibre mats (LKB-Wallac, Turku, Finland) using a Mach 111 harvester 96 (Tomtec, Orange, N.J., USA). [$^3$H]-Thymidine incorporation is determined using a Microbeta liquid scintillation counter (LKB-Wallac). Test wells containing antigen are considered positive when the δcpm>1000 and the Stimulation Index (SI)>3, where SI=CPM antigen containing culture/CPM culture without antigen.

Results

The response of T cell clone MS60:D2 to presentation of nested MBP peptides in the region 131–158 is shown in FIG. 1. Peptides 134–148, 135–149, 136–150, 137–151, 138–152, 139–153 and 140–154 are defined as apitopes as they could be presented by fixed APC to T cells without further processing.

Figure 2:
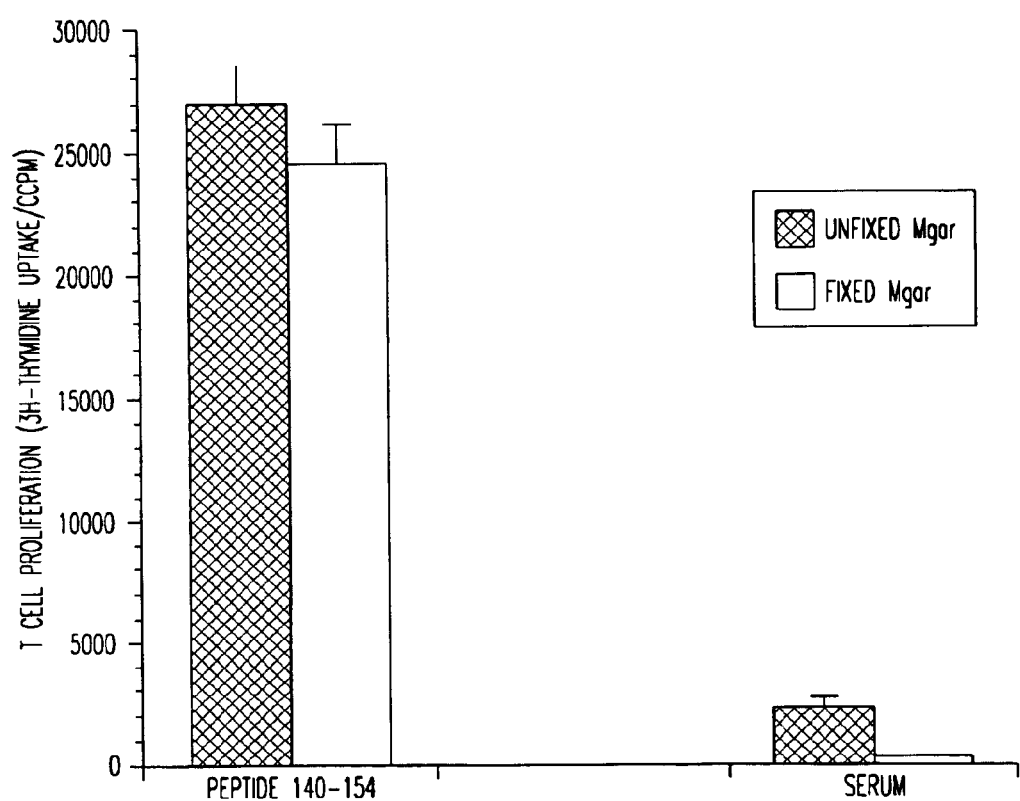
FIG. 2 shows the response of T cell clone N5 to presentation of MBP peptide 140–154 by APC.

The response of T cell clone N5 to presentation of peptide 140–154 is shown in FIG. 2. This further confirms that peptide 140–154 can be presented by fixed APC without further processing.

Example 2

Identification of the Minimum Epitope Recognised by T Cell Clones N5 and MS60:D2

Live Mgar cells were incubated with overlapping peptides from MBP region 136–157 in serum or serum alone, together with N5 T cells. T cell proliferation was measured by $^3$H-thymiding uptake.

Figure 3:
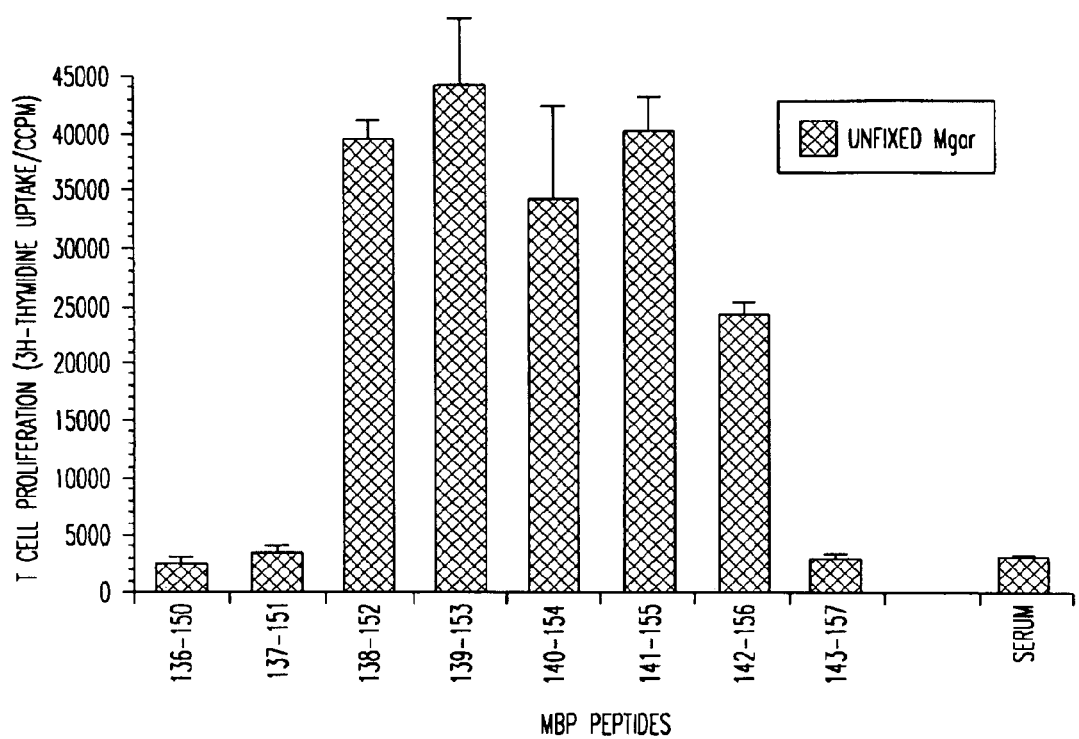
FIG. 3 shows the response of T cell clone N5 to presentation of nested MBP peptides in the region 136–157 by APC.

The results are shows in FIG. 3. The minimal epitope recognised by T cell clone N5 is MBP 142–152.

A similar experiment was performed for T cell clone MS60:D2 (FIG. 1, unfixed Mgar). The minimal epitope recognised by this T cell clone is MBP 140–148.

Various modifications and variations of the described methods and system of the invention will be apparent to those skilled in the art without departing from the scope and spirit of the invention. Although the invention has been described in connection with specific one embodiments, it should be understood that the invention as claimed should not be unduly limited to such specific embodiments. Indeed, various modifications of the described modes for carrying out the invention which are obvious to those skilled in chemistry or biology or related fields are intended to be covered by the present invention.

Example 3

Induction of Tolerance in a HLA:DR2 Transgenic Mouse

An apitope of the present invention, when presented by an MHC molecule, can induce immunological tolerance in a humanized mouse model of multiple sclerosis. APITOPE-MS-6 is a peptide selected from within T-cell epitopes of myelin basic protein (MBP) corresponding to MBP 140–154 (SEQ ID NO:7). The apitope is presented by MHC Class II on an antigen presenting cell without being processed. The mouse model was transgenic for the human MHC molecule HLA:DR2 (DRB1*1501) (Madsen et al. (1999) Nature Genetics 23:343–347).

An apitope bound to a MHC Class II molecule on the surface of an immature antigen presenting cell (APC) provides the first signal (signal 1) for the T-cell via the T cell receptor. Unlike mature APC (such as macrophages, B cells and dendritic cells), immature APC do not express co-stimulatory molecules such as CD-80, CD-86, which provide the second signal (signal 2) for T-cell activation. When T cells receive signal 1 in the absence of signal 2 they become anergic rather than activated. Anergic T cells are unable to respond to subsequent antigenic challenge. Apitopes do not require further processing, therefore can bind directly to MHC Class II on immature APC and will be presented to T cells without costimulation leading to T-cell anergy and tolerance. As the immune system contains a far greater abundance of immature than mature APC (Summers et al. (2001) AM. J. Pathol. 159:285–295), administration of an apitope to a mouse will induce anergy/tolerance rather than T-cell activation.

The induction of anergy or changes in the CD4+ T-cell population in a mouse following administration of an apitope may be monitored by a reduction in T-cell proliferation when challenged with the antigen in vivo.

Methods

Antigens

MBP peptide 140–154 (SEQ ID NO:7) was synthesised using L-amino acids and standard F-moc chemistry on an Abimed AMS 422 multiple peptide synthesizer (Abimed, Langenfeld, Germany). The sequence of MBP peptide 140–154 is GFKGVDAQGTLSKIF (SEQ ID NO:7). Purified Protein Derivative of *Mycobacterium tuberculosis* (PPD) (Veterinary Laboratories, Addlestone, Surrey) was used at a concentration of 50 ugml$^{-1}$ in lymphocyte proliferation assays.

Mice and Tolerance Induction

HLA:DR2 transgenic were bred in isolators and housed in a specific pathogen-free facility at Bristol University. Within each treatment group, mice were both age (8–12 weeks) and sex matched. Mice were pre-treated with 100 ug of MBP peptide 140–154 (SEQ ID NO:7) in 25 ul of phosphate buffered saline (PBS) or 25 ul PBS alone intranasally (i.n) on days −8, −6 and −4 prior to immunisation on day 0.

Mice were immunised subcutaneously at the base of the tail and hind limb with 100 ul of an emulsion consisting of an equal volume of Complete Freund's Adjuvant (CFA) and PBS containing 200 ug MBP140–154 (SEQ ID NO:7) and 400 ug heat-killed *Mycobacterium tuberculosis*, strain H37RA(Difco, Detroit, Mich.). A control group of mice, previously treated with PBS i.n., were immunised without peptide.

Intranasal pre-treatment followed by immunisation gave rise to three groups of mice: Group A was tolerised with PBS and immunised with MBP 140–154 (SEQ ID NO:7) (7 mice); Group B was tolerised with MBP 140–154 (SEQ ID NO:7) and then immunised with the same peptide (7 mice); and Group C was both tolerised and immunised with PBS.

Lymph Node Proliferation Assays

After 10 days, draining popliteal and inguinal lymph nodes were removed aseptically. The nodes were disaggregated, washed and resuspended in X-Vivo 15 medium (BioWhittaker, Maidenhead, UK) supplemented with 5×10$^{-5}$M 2-mercaptoethanol and 4 mM L-glutamine. Cells were plated in triplicate at 5×10$^5$ cells well$^{-1}$ and cultured with or without varying concentrations of MBP peptide 140–154 (SEQ ID NO:7) (1–150 ugml$^{-1}$) for 72 hours. To check for successful immunisation of mice, lymph node cells were plated with PPD (50 ugml$^{-1}$) as described above. Cultures were pulsed for the final 16 hours with 0.5 uCi [$^3$H]-Thymidine. Cells were harvested and T-cell proliferation was expressed as Stimulation Index (SI): corrected counts per minute (ccpm) antigen containing culture/ccpm culture without antigen.

Results

Figure 4A:
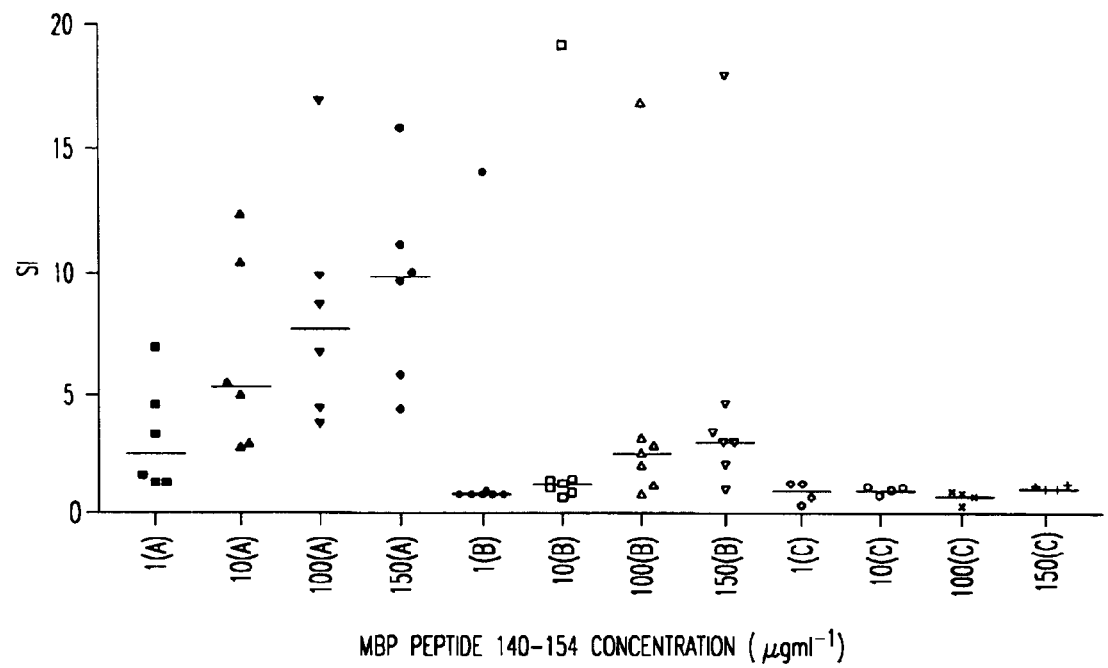
FIG. 4 shows the proliferative response of lymph node cells following tolerization with MBP 140–154 (SEQ ID NO:7). HLA-DR2 transgenic mice were pre-treated intranasally with either MBP 140–154 (Group B) or PBS (groups A and C) prior to immunising with MBP 140–154 (A and B) or PBS (C) in CFA as described in Example 3, Methods. After 10 days lymph cells were isolated and stimulated with either MBP 140–154, at 1–150 µgml$^{-1}$ (a) or with purified protein derivative (PPD) of *Mycobacterium tuberculosis* (PPD) antigen (50 µgml$^{-1}$; b). The lymphocyte proliferative response was measured by [$^3$H]-Thymidine uptake and expressed as a Stimulation Index (SI).

Mice that were pre-treated i.n. with PBS and then immunised with MBP peptide 140–154 (Group A) responded to antigenic stimulation when re-challenged with MBP140–154 in a dose dependent manner (FIG. 4a). With increasing concentration of peptide, the SI, a measure of lymphocyte proliferation, increased from a median of 2.5 to 10. All the mice in this group demonstrated that PBS administered intranasally could not induce tolerance to MBP 140–154 (SEQ ID NO:7). In contrast, intranasal pre-treatment with MBP 140–154 (SEQ ID NO:7) had a profound effect on the proliferative response of lymphocytes stimulated with this peptide; lymphocytes from Group B mice were unable to respond to any significant degree, even at the high peptide concentration of 150 ugml$^{-1}$ (SI median 3, FIG. 4a). The marked reduction in proliferation in Group B as compared with Group A is evident even when one of the mice pre-treated with MBP 140–154 (SEQ ID NO:7) failed to show induction of tolerance, (SI values 12–15 over peptide concentration range, FIG. 4a), was included in the mean calculation of Group B SI. The data shows that peptide MBP 140–154 (SEQ ID NO:7), which is an apitope, induced tolerance in lymphocytes from HLA-DR2 mice.

Figure 4B:
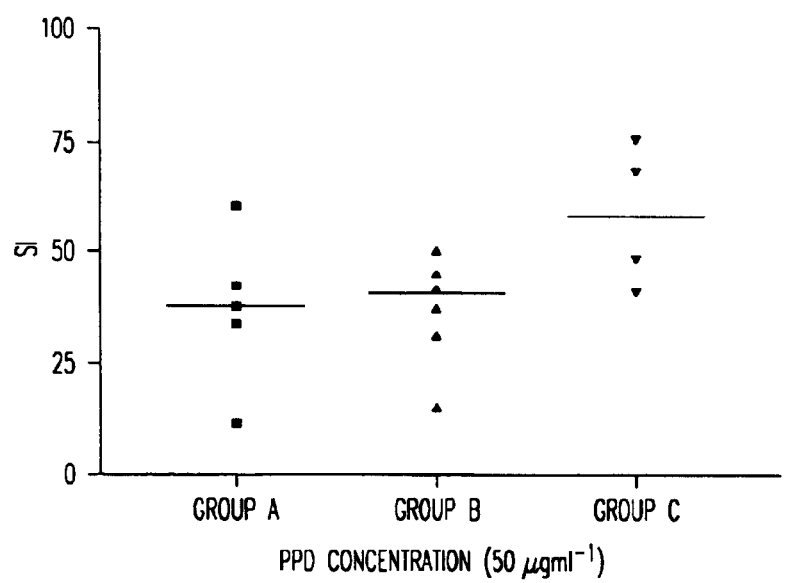

Lymphocytes extracted from mice which had been pre-treated and immunised with PBS (Group C) failed to show any response to MBP 140–154 suggests (FIG. 4a), although they elicited an excellent response to PPD and were therefore immunised against the PPD antigen (FIG. 4b). This lack of response to MBP peptide within Group C confirms that the proliferative response seen in Group A was indeed a response to immunisation with MBP 140–154 (SEQ ID NO:7), and that the responses to both MBP 140–154 (SEQ ID NO:7) and PPD in control Groups A and C are antigen specific. As the proliferation to MBP 140–154 (SEQ ID NO:7) was antigen specific, induction of tolerance to this molecule is also specific.

CONCLUSION

An MBP peptide of the invention, e.g., SEQ ID NO:7, that does not require processing and binds to HLA:DR2 MHC Class II molecules, can induce tolerance when administered intranasally.

All publications mentioned in the above specification are herein incorporated by reference.

What is claimed is:

1. An isolated and purified peptide consisting of the sequence SEQ ID NO:1, SEQ ID NO:2, SEQ ID NO:3, SEQ ID NO:4, SEQ ID NO:5, SEQ ID NO:6 or SEQ ID NO:7.

2. The peptide of claim 1 that is SEQ ID NO:7.

3. A pharmaceutical composition comprising the peptide of claim 1.

4. The composition of claim 3 in combination with a pharmaceutically acceptable carrier.

5. A therapeutic composition comprising an effective, immunosuppressive amount of an isolated and purified peptide consisting of the sequence SEQ ID NO:1, SEQ ID NO:2, SEQ ID NO:3, SEQ ID NO:4, SEQ ID NO:5, SEQ ID NO:6 or SEQ ID NO:7.

6. The composition of claim 5, wherein the amount is effective to induce immunological tolerance in a mammal.

7. The composition of claim 5, wherein the peptide is SEQ ID NO:7.

8. The composition of claim 5, in combination with a pharmaceutically acceptable carrier.

9. A method for treating or preventing multiple sclerosis in a subject in need thereof comprising administering to the subject an effective amount of an isolated and purified peptide consisting of SEQ ID NO:7.

10. The method of claim 9, wherein the peptide is administered intranasally.

11. The peptide of claim 1 that is SEQ ID NO:1.

12. The peptide of claim 1 that is SEQ ID NO:2.

13. The peptide of claim 1 that is SEQ ID NO:3.

14. The peptide of claim 1 that is SEQ ID NO:4.

15. The peptide of claim 1 that is SEQ ID NO:5.

16. The peptide of claim 1 that is SEQ ID NO:6.

* * * * *

UNITED STATES PATENT AND TRADEMARK OFFICE
CERTIFICATE OF CORRECTION

PATENT NO. : 7,071,297 B2  Page 1 of 1
APPLICATION NO. : 10/900032
DATED : July 4, 2006
INVENTOR(S) : Wraith et al.

It is certified that error appears in the above-identified patent and that said Letters Patent is hereby corrected as shown below:

Column 16, line 37, in Claim 9, after "treating" delete "or preventing".

Signed and Sealed this

Twenty-first Day of November, 2006

JON W. DUDAS
*Director of the United States Patent and Trademark Office*